United States Patent [19]

Chan

[11] Patent Number: 5,612,213
[45] Date of Patent: Mar. 18, 1997

[54] METHOD OF SELECTING MAMMALIAN CELL LINES HAVING IMPROVED PRODUCTIVITY

[75] Inventor: Sham Y. Chan, El Sobrante, Calif.

[73] Assignee: Bayer Corporation, Berkeley, Calif.

[21] Appl. No.: 333,706

[22] Filed: Nov. 3, 1994

Related U.S. Application Data

[63] Continuation-in-part of Ser. No. 75,209, Jun. 10, 1993, abandoned.

[51] Int. Cl.$^6$ .............................. C12N 5/06; C12N 15/63; C12P 21/06; C12Q 1/68
[52] U.S. Cl. .................... 435/6; 435/69.1; 435/320.1; 435/325; 435/366; 435/369
[58] Field of Search .................. 435/6, 69.1, 240.2, 435/320.1; 536/24.1; 935/23, 27, 41, 43, 60, 84

[56] References Cited

U.S. PATENT DOCUMENTS

| | | | |
|---|---|---|---|
| 4,740,461 | 4/1988 | Kaufman | 435/69.1 |
| 4,965,199 | 10/1990 | Capon et al. | 435/69.6 |
| 5,079,159 | 1/1992 | Kaufman | 435/226 |

FOREIGN PATENT DOCUMENTS 0260148  3/1988  European Pat. Off. .

OTHER PUBLICATIONS

Huang, et al., Nucleic Acid Res. (1990) 18:937–947.
Kellems, Curr. Op. Biotech (1991) 2:723.
Kaufman, et al., Mol. Cell. Biol. (1985) 5(7): 1750–1759.
Walls, et al., Gene (1989) 81:139–149.
Okamoto, et al., Biotechnol (1990) 8:550–553.
Dolph, et al., J. Virol. (1990) 64(6):2669–2677.

*Primary Examiner*—George C. Elliott
*Assistant Examiner*—Thanda Wai
*Attorney, Agent, or Firm*—James A. Giblin

[57] ABSTRACT

A method of selecting transfected cell lines for heterologous protein expression from a population of cells some of which include an endogenous sequence for an amplificable marker and some of which do not include the sequence. The method is based on a minimum amplifiability index which, contrary to current practice, focuses cell lines having relatively low productivity prior to amplification. Transfected cell lines selected with the instant invention produce greater amounts of heterologous protein than cells selected according to the prior art. In one embodiment, the amplifiability index is used to select for further amplification a cell line transfected with a vector containing the coding sequence for human Factor VIII.

16 Claims, 7 Drawing Sheets

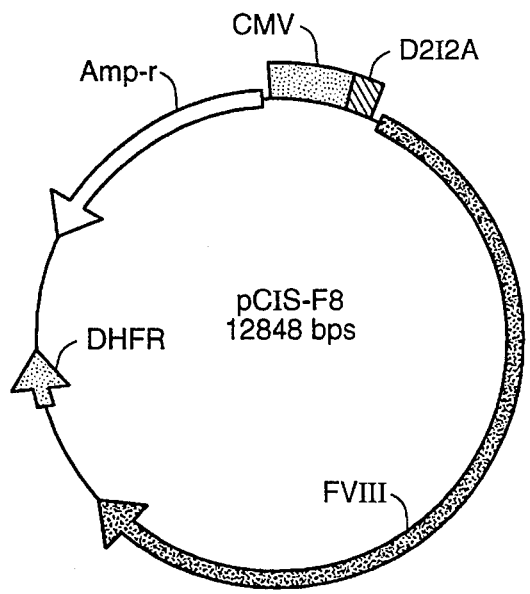
FIG._1A
(PRIOR ART)
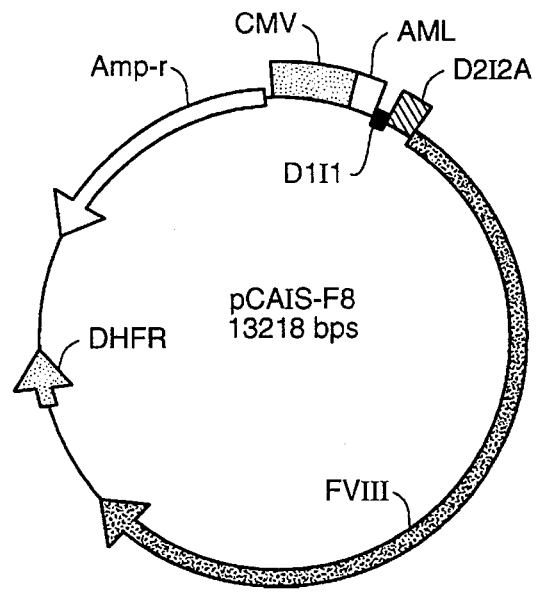
FIG._1B
FIG._2A
(PRIOR ART)
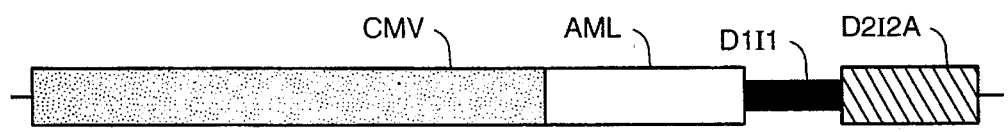
FIG._2B

```
CCGCGGTCCT  CCTCGTATAG  AAACTCGGAC  CACTCTGAGA  CGAAGGCTCG  CGTCCAGGCC   60
AGCACGAAGG  AGGCTAAGTG  GGAGGGGTAG  CGGTCGTTGT  CCACTAGGGG  GTCCACTCGC  120
TCCAGGGTGT  GAAGACACAT  GTCGCCCTCT  TCGGCATCAA  GGAAGGTGAT  TGGTTTATAG  180
GTGTAGGCCA  CGTGACCGGG  TGTTCCTGAA  GGGGGGCTAT  AAAAGGGGGT  GGGGGCGCGT  240
TCGTCCTCAC  TCTCTTCCGC  ATCGCTGTCT  GCGAGGGCCA  GCTGTTGGGG  TGAGTACTCC  300
CTCTCAAAAG  CGGGCATGAC  TTCTGCGCTA  AGATTGTCAG  TTTCCAAAAA  CGAGGAGGAT  360
TTGATATTCA  CCTGGCCCGC  GG                                              382
```

FIG._3

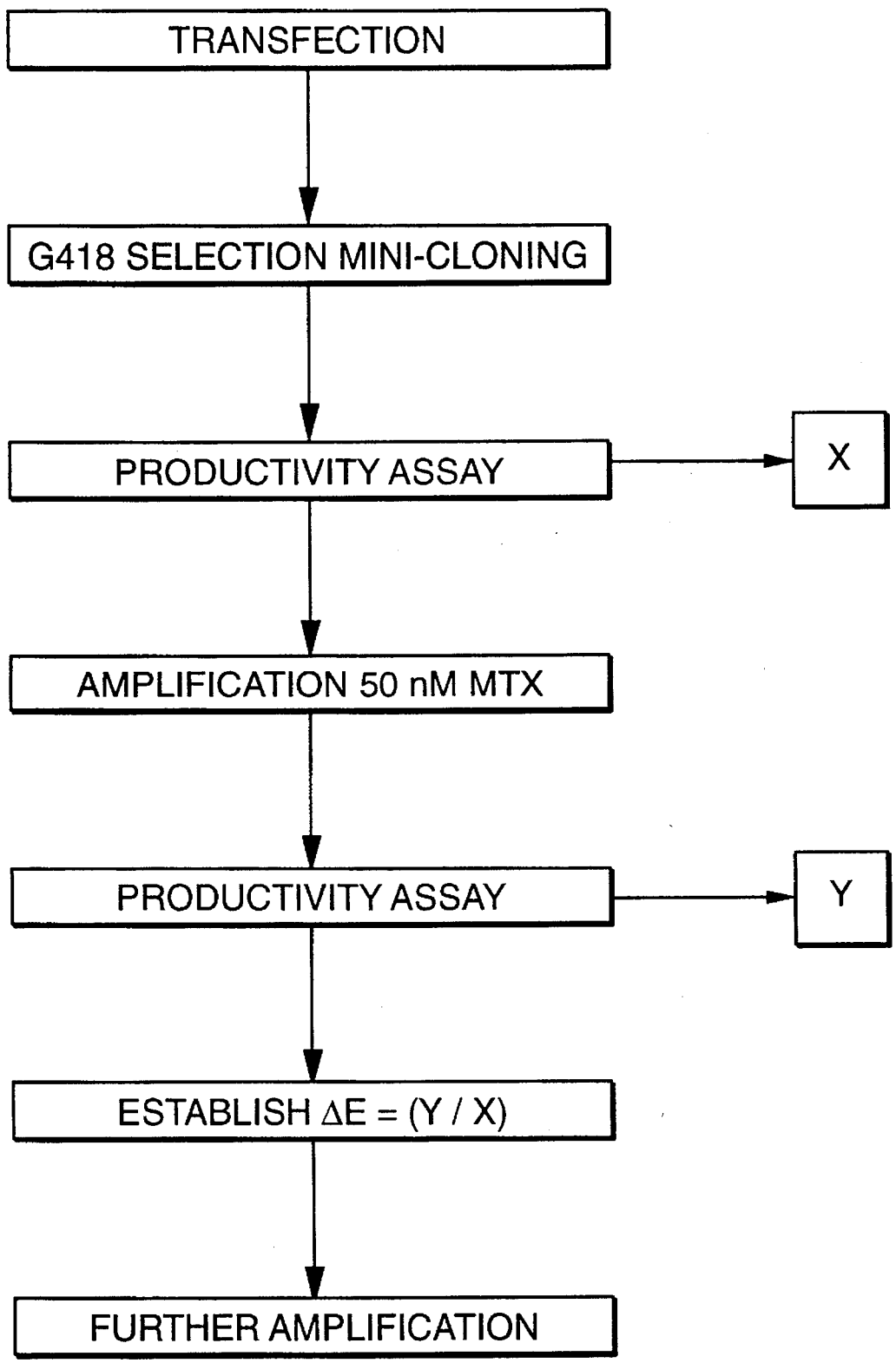
FIG._4

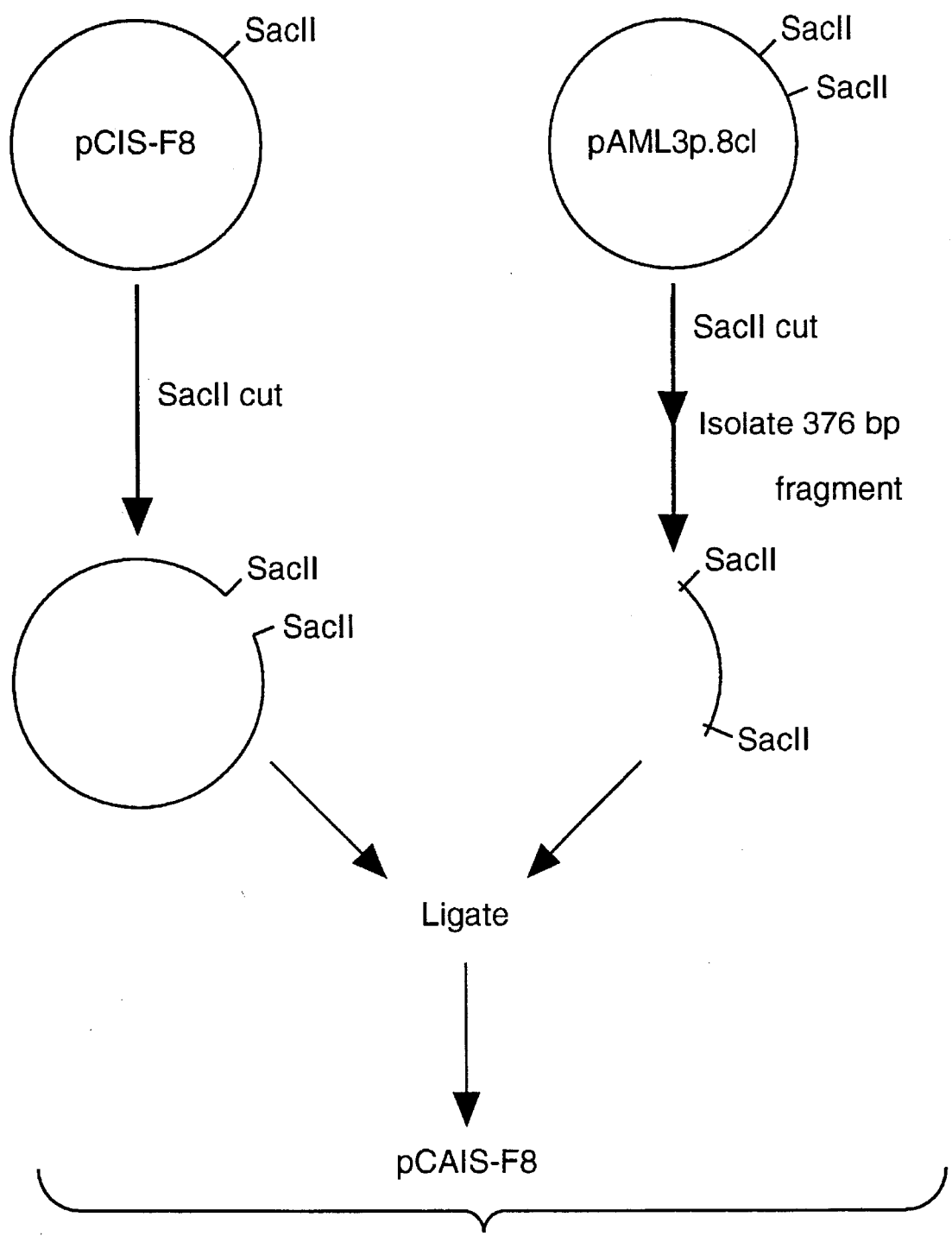
FIG._5

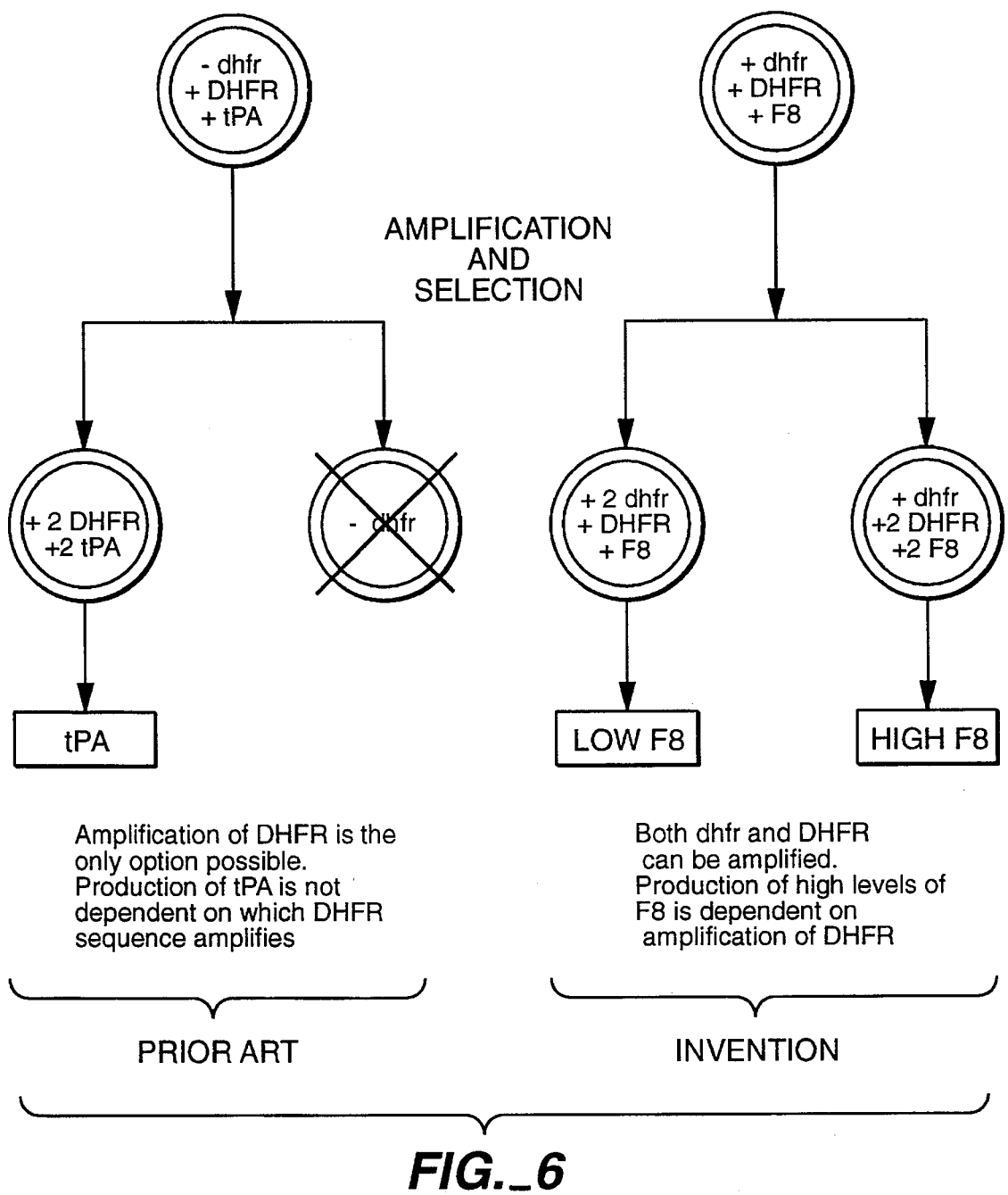
FIG._6

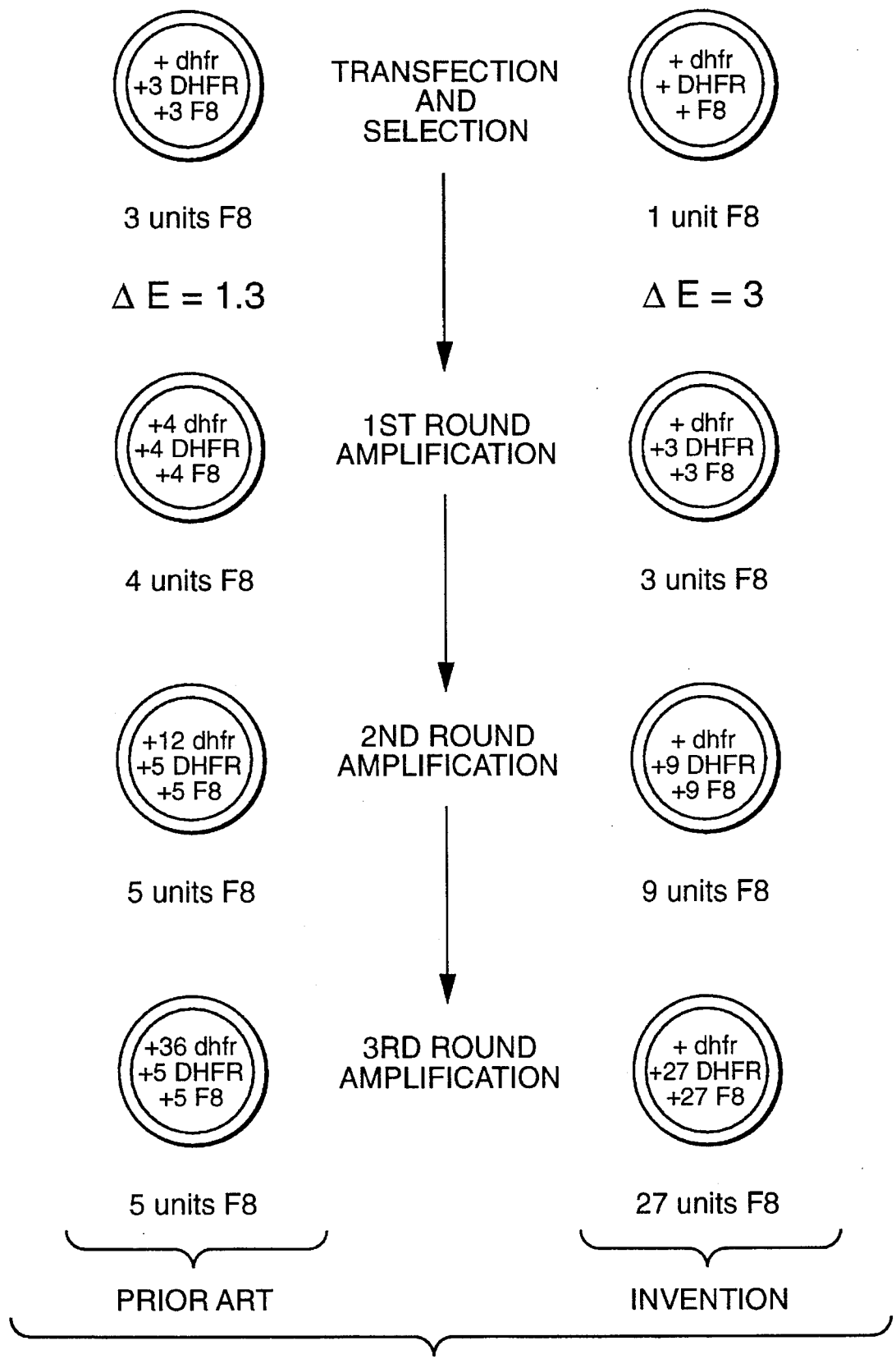
FIG._7

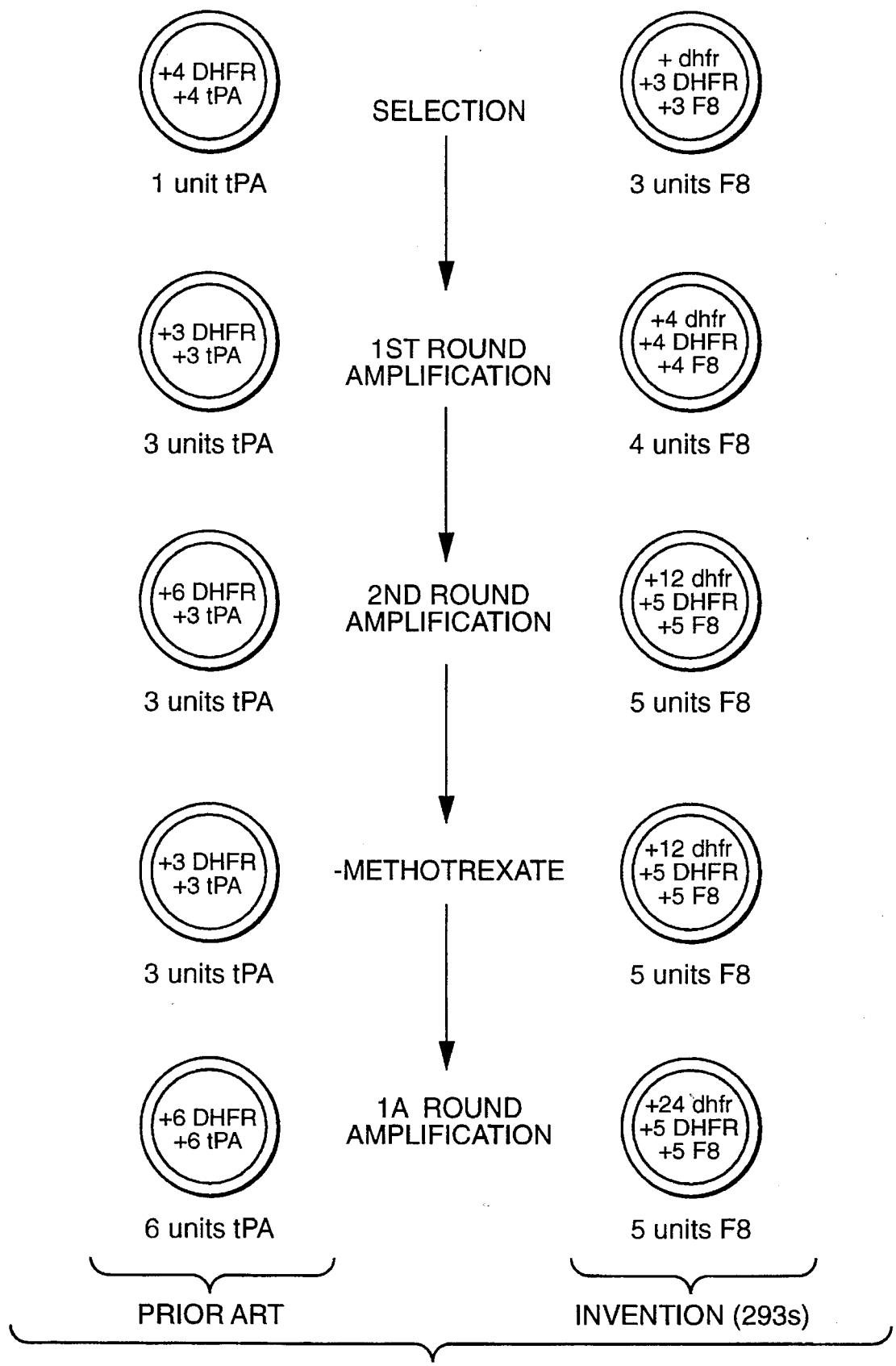
FIG._8

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
      ( A ) LENGTH: 382
      ( B ) TYPE: nucleic acid
      ( C ) STRANDEDNESS: single
      ( D ) TOPOLOGY: linear ( x i ) SEQUENCE DESCRIPTION: SEQ ID NO:1:

```
CCGCGGTCCT  CCTCGTATAG  AAACTCGGAC  CACTCTGAGA  CGAAGGCTCG  CGTCCAGGCC       60
AGCACGAAGG  AGGCTAAGTG  GGAGGGGTAG  CGGTCGTTGT  CCACTAGGGG  GTCCACTCG       120
TCCAGGGTGT  GAAGACACAT  GTCGCCCTCT  TCGGCATCAA  GGAAGGTGAT  TGGTTTATA       180
GTGTAGGCCA  CGTGACCGGG  TGTTCCTGAA  GGGGGGCTAT  AAAAGGGGT   GGGGGCGCG       240
TCGTCCTCAC  TCTCTTCCGC  ATCGCTGTCT  GCGAGGGCCA  GCTGTTGGGG  TGAGTACTC       300
CTCTCAAAAG  CGGGCATGAC  TTCTGCGCTA  AGATTGTCAG  TTTCCAAAAA  CGAGGAGGA       360
TTGATATTCA  CCTGGCCCGC  GG                                                  382
```

METHOD OF SELECTING MAMMALIAN CELL LINES HAVING IMPROVED PRODUCTIVITY

This is a Continuation-In-Part of patent application Ser. No. 08/075,209, filed Jun. 10, 1993 (now abandoned).

BACKGROUND OF THE INVENTION

1. Field

This invention relates generally to the production of biologically active proteins from genetically engineered mammalian cell lines. Specifically, the invention is concerned with cell selection method which enhances cell line productivity and a novel vector for increased expression of recombinant Factor VIII from mammalian cells.

2. Prior Art

Gene amplification is a strategy which has been broadly applied to increase protein production in mammalian cells. A transcription unit (cDNA) encoding a protein of interest is normally linked covalently to an amplifiable marker. The transcription unit and marker are then co-transfected into appropriate cells, followed by selection and amplification as discussed below.

I Amplification

One of the more widely used gene transfection and amplification strategies utilizes dihydrofolate reductase (DHFR) expression vectors in conjunction with DHFR-deficient Chinese hamster ovary (CHO) cells (Kellems, *Curr. Op. Biotech.*, 2:723 (1991)). A number of commercially valuable proteins including tissue plasminogen activator (tPA), erythropoietin, and Factor VIII have been produced by this strategy (see U.S. Pat. No. 4,740,461 to Kaufman and in Kaufman, et al., *Mol. Cell. Biol.*, 5(7):1750 (1985)). Because DHFR is not present in the host cells used for transfection, methotrexate (MTX) can be utilized to amplify vector-supplied dhfr and the linked sequence for the protein of interest. As used herein, cell lines containing the exogenous (introduced) marker are designated using upper case letters (e.g., DHFR or DHFR+). The endogenous markers are designated using lower case letters (e.g., dhfr or dhfr).

If the vector-supplied DHFR has disassociated from the coding sequence of the protein of interest, a rest period with MTX-free medium will enable the cells to eject the dissociated and non-integrated DHFR. When MTX is returned to the medium, the stably integrated dhfr will amplify, thereby co-amplifying the coding sequence of the protein of interest.

II Transfection in dhfr+ Cell Lines

In cell lines containing endogenous dhfr, including most if not all commercially available human cell lines, success in the amplification of sequences coding recombinant proteins has been limited. This may be because the endogenous dhfr can amplify in the presence of MTX without co-amplification of the sequence coding for the protein of interest.

U.S. Pat. No. 4,965,199 (Capon, et at., 1990) describes a process for producing Factor VIII in dhfr+ baby hamster kidney cells (BHK-21). This process involves (i) the co-transfection of host cells with a DNA sequence coding for Factor VIII linked to a second DNA sequence encoding DHFR, and a selectable marker conferring neomycin resistance, (ii) selection of transfectants in a selective medium containing G418, and (iii) amplification of G418 resistant cells in media containing increasing amounts of methotrexate.

For proteins of low molecular weight, the possible disjunction in amplification between DHFR and the protein of interest may not be a problem. A few copies of the sequence of a low molecular weight protein may be all that is necessary for adequate production by the host cell. Walls, et at. (*Gene*, 81:139 (1989)) have reported on the use of DHFR/MTX co-amplification strategy to express functional Protein C in human 293 cells. Okamoto, et al. (*Biotechnol.*, 8:550 (1990)) have also described the amplification and expression of Granulocyte Colony Stimulating Factor (GM-CSF) in human lymphoid cells.

The use of human cell lines as a host for the production of complex or large recombinant human proteins would obviate immunogenicity problems that may be observed when the host cells of another mammalian species are used. But to successfully utilize human cell lines (which are dhrf+) as hosts for larger proteins where increased copy number may be important for production, a process for selecting and amplifying heterologous protein production must exclude those cells in which dhfr preferentially amplifies over vector-supplied dhfr.

III Vector Construction

Despite recent advances in recombinant DNA techniques, the derivation of recombinant cell clones with high productivity for large and complex therapeutic proteins such as Factor VIII in human cell lines has remained difficult. European patent application No. 0260148 (Gorman, published Sep. 17, 1987) and incorporated herein by reference describes the construction of an expression vector (pCIS-F8) having an augmenting (stabilizing) sequence downstream of a promoter and upstream of the DNA encoding Factor VIII. The vector was constructed with a cytomegalovirus (CMV) promoter and enhancer, a cDNA encoding Factor VIII and a 3' terminating sequence. In the absence of this augmenting sequence, expression of Factor VIII was not observed in any cell types tested. In cells containing the augmenting sequence, and after amplification in 1 μM MTX, Factor VIII production remained low (E.P. App. No. 0260148, pg. 13). To select cells for amplification, Gorman compared transient expression of Factor VIII 36–48 hours after transfection with expression after selection but before amplification (E.P. App. No. 0260148, pg. 12).

Huang and Gorman (*Nucleic Acids Research*, 18(4):937 (1990)) described the construction and use of vectors containing the SV40 promoter, the AML donor splice site and intervening sequence, and the Ig variable region acceptor. They stressed that the presence of the intervening sequence was important for increased production. Part of the first sequence of the tripartite leader was missing in their construct. Gorman in E.P App. No. 0260148 described the use of the CMV promoter and donor splice site and the Ig variable region acceptor. The application claimed that up to two promoters/donors/acceptors could be used but there was no claim that two donors and one acceptor would be beneficial. In contrast to Huang et al. and Dolph (infra), the specification did not disclose any improvement in protein productivity with the use of tripartite leaders or intervening sequences.

Dolph, et al. (*J. Virol.*, 64(6):2669 (1990)) found that if the second and third tripartite leaders were absent, mRNA stability would decrease. Therefore one would not expect to see increased production using a vector where only the first tripartite leader sequence was present. However, quite unexpectedly, I established a high producing cell line transfected with a novel modified vector containing the first tripartite leader sequence. In addition to the first tripartite leader sequence, the novel vector contained two promoters and one acceptor, and a small portion of the first intervening sequence.

In an initial experiment, I co-transfected human 293s cells with pCIS-F8 and a plasmid expression vector which confers neomycin resistance. While I obtained recombinant cell lines with moderate productivity (0.1–0.2 μU/c/d) for Factor VIII, numerous attempts to amplify a large number of populations and clones from various transfection experiments failed to generate high producing clones after extensive amplification in MTX (up to 1–2 μM) as described by U.S. Pat. Nos. 4,4740,461 (Kaufman) and 4,965,199 (Capon, et al.).

To solve this dilemma, I developed a method of selecting cell populations based on a novel minimum amplifiability index which significantly increased the expression level of heterologous proteins. In an illustrative example, I transfected the novel modified vector described above, including the coding sequence for coagulation Factor VIII, into a human cell line and then used the minimum amplifiability index to select a cell line of high Factor VIII expression.

SUMMARY OF INVENTION

This disclosure describes an improved process to select amplifiable cell populations for expressing a desired protein so that continuous production of the protein can be achieved and with higher productivity. The process is especially useful for selecting from a population of cells having cells which include a sequence for an amplificable marker and cells which do not include the sequence for the same marker.

A preferred amplifiable marker is DHFR although other markers such as glutamine synthetase (GS) and multidrug-resistance (MDR) can be substituted. The cell to be transfected can be any mammalian cell and need not be dhfr+. Cell lines that are known to integrate selection genes into their chromosomal DNA are best; for example, human embryonic kidney (293s), Chinese hamster ovary (CHO), baby hamster kidney (BHK-21), myeloma, and hepatoma lines such as HepG2 cells and the like.

The productivity of a transfected mammalian cell line can be enhanced by establishing a minimum amplifiability index which, contrary to current practice, focuses on choosing cell lines having relatively low productivity after an initial selection and mini-cloning, but prior to amplification. According to the disclosure, selected cells must have an amplifiability index ($\Delta E = Y/X$) > 3 where X = production of the cells before the first amplification and Y = production of the cells after the first amplification.

Cell populations with a minimum amplification index of greater than three are chosen for further amplification to ensure that the increase in heterologous protein production is due to an increase in productivity per cell and not due to slight increases in cell number. The cell populations are assayed for Factor VIII productivity when they are 50–60% confluent by visual determination. Because of the inherent inaccuracy of the determination, there will be some difference in cell number at the time of assay. Also if an amplifiability index of less than three is chosen, the number of cell populations to be screened and further amplified increases ten-fold. The higher number is clearly an unmanageable number of cell lines.

A novel vector, the use of which illustrates this disclosure, comprises a protein coding sequence, a first promoter and a downstream donor intron, the first promoter and downstream donor intron being located between a second promoter and a donor intron acceptor. In addition, a termination sequence and a polyadenylation site are downstream of the coding sequence. In one preferred embodiment, the sequence codes for Factor VIII (also known as FVIIIC or FVIII:C) and the vector is pCAIS-F8. The coding sequence can also be for Factor VIII derivatives, variants, or fragments (see, for example, U.S. Pat. No. 5,045,455). The vector is used to introduce the appropriate DNA coding sequence for an heterologous protein into mammalian cells to increase protein expression by the cells.

Also on this vector is a DNA sequence coding for DHFR. For transfection, two vectors are needed; the vector containing Factor VIII and DHFR, and another vector containing a DNA sequence coding for neomycin resistance. However, the use of two vectors is illustrative only, and one skilled in the art would recognize the amplifiability index could be used with three sequences in one vector or each sequence in a separate vector.

BRIEF DESCRIPTION OF THE FIGURES

FIG. 1a shows the prior art vector pCIS-F8.

FIG. 1b shows the vector pCAIS-F8 of this disclosure.

FIG. 2a shows a linear map of the CMV promoter donor$_2$-intron$_2$-acceptor (D2I2A) of FIG. 1a.

FIG. 2b shows a linear map of the location of AML promoter and donor$_1$-intron$_1$ in relation to CMV promoter and donor$_2$-intron$_2$-acceptor of FIG. 1b.

FIG. 3 shows the nucleotide sequence of adeno major late promoter and its intron (SEQ ID NO: 1).

FIG. 4 is a flow chart illustrating the overall selection process of this disclosure and the calculation of $\Delta E$.

FIG. 5 is a flow chart illustrating the construction scheme of the vector pCAIS-F8.

FIGS. 6, 7, and 8 compare the selection process of this invention with prior art processes.

SPECIFIC EMBODIMENTS

Example 1. Construction of expression vectors.

Expression vectors pCIS-F8 and pSV2-neoBa16 were constructed as described in European Patent Application No. 0260148. The improved expression vector (designated pCAIS-F8) was constructed by isolating a 382 bp SacII fragment from pAML3p.8cl (as described in U.S. Pat. No. 4,965,199) which contains the adeno major late promoter and the immediate 3' intron sequence including the complete first tripartite leader sequence (+1 to +132 with respect to the CAP site, FIG. 2) and inserting it into the SacII site of the known vector pCIS-F8 using standard recombinant DNA techniques (Maniatis, 1990). From the results indicated in Table 1, it can be seen by comparing the Factor VIII production between pCIS-F8 and pCAIS-F8 with either of the selection methods, the immediate 3' intron sequence appears to be an augmenting sequence which stabilizes mRNA transcription. Because isolation of plasmid vectors from transformed bacteria is technically easy, the pCAIS-F8 vector in E. coli and it was deposited with the ATCC on Aug. 24, 1994 and assigned ATCC designation ATCC 69685.

Briefly, the 382 bp fragment was gel-purified after digesting 50 μg of pAML3p.8cl with SacII. This fragment was then ligated to pCIS-F8 which had been linearized with SacII. After 4 hours of ligation at 20° C., 50 ng of the ligation mix was used to transform E. coli DH5α. Successful cloning of the AML promoter and intronic sequences was confirmed by sequencing (FIG. 2). The construction scheme of the vector is shown in FIG. 5.

TABLE 1

Factor VIII productivity of amplified clones of 293s cells transfected with various expression vectors.

| Vectors (1 µM) | Screening Method | Productivity of clones** (µU/c/d) |
|---|---|---|
| pCIS-F8 | Traditional* | 0.1–0.25 |
| pCIS-F8 | ΔE | 0.7–1.0 |
| pCAIS-F8 | Traditional* | 0.15–0.3 |
| pCAIS-F8 | ΔE | 1.3–1.5 |

*Cells showing highest productivity after G418 selection were chosen for further amplification in MTX
**A total of 10–12 clones were evaluated by productivity after attaining resistance to 1 µM MTX.

As shown in this disclosure, the ΔE index is a useful indicator to identify potentially high producing cell populations.

Example 2. Derivation of stable cell clones with high productivity.

Production cell lines were established by co-transfecting $5 \times 10^5$ cells with 10 µg of pCIS-F8 or pCAIS-F8 and 10 µg of pSV2-neoBa16 using the lipofection method according to manufacturer's instruction (Gibco). A typical transfection experiment involved $2.5 \times 10^6$ cells. Multiple transfections were normally done simultaneously. Two days following transfection, cells were trypsinized, seeded into a 48-well plate (CoStar, growth area=100 mm²), and grown in a selective medium (DMEM/F12, weight ratio=1:1) containing G418 (400/µg/mL). The Factor VIII productivity of the G418-resistant cells were assayed at approximately 50% confluence (about 3 weeks after the onset of selection) by a chromogenic substrate method according to manufacturer's instructions (Coatest, Kabi). The cells were then allowed to grow to confluence in a medium (DMEM/F12, 1:1 deficient in glycine, hypoxanthine, and thyroidinc) containing 50 nM MTX. This initial amplification step normally takes about 3 weeks. The MTX-resistant cells were then assayed for Factor VIII productivity.

CELL LINE SELECTION PROCESS

A ΔE index for each population was then determined. A ΔE index is defined as ΔE=Y/X where X = productivity before 50 nM MTX amplification, and Y = productivity after 50 nM MTX selection. The cell populations were 50–60% confluent at each productivity determination. A typical transfection would involve the screening of 220–440 populations of transfected cells. Cell populations with ΔE>3 were further subcloned and amplified in the next higher level of MTX (100 nM).

The traditional selection procedure involves the subculturing of 1 population (approximately $1 \times 10^5$) of cells into 96 subpopulations (96-well plate, growth area 32 mm²). The cells are grown to confluence in 100 nM MTX and assayed for Factor VIII productivity. The population with the highest productivity is then subjected to the same regiment of clonal enrichment under amplification in the next higher level of MTX (200 nM). The same regiment of selection is repeated until a steady high level of protein productivity is reached. For 293s cells, maximum productivity is typically achieved at 1/ µM MTX. Further amplification in higher levels of MTX does not increase protein productivity. Single cell clones are then obtained by limiting dilution cloning in the presence of 50 nM MTX.

FIG. 6 demonstrates the prior art is inadequate when the transfected cell lines contain endogenous dhfr. In these cell lines, there is a possibility that the dhfr may preferentially amplify over the vector-supplied DHFR. If DHFR does not amplify, the Factor VIII coding sequence does not amplify and productivity remains low. FIG. 7 is a schematic showing the importance of the amplifiability index. Selecting cell lines with a high amplifiability index ensures that the chosen cell lines contain vector-supplied DHFR which is amplifying preferentially over endogenous dhfr.

FIG. 8 indicates that the prior art method of Kaufman where MTX is removed from the media for a rest period will not function with cells with endogenous dhfr. The removal of MTX from the media allows the cells without endogenous dhfr to eject non-genomic, disassociated DHFR. MTX is then re-introduced for further amplification of integrated DHFR and the coding sequence. In dhfr+ cell lines, dhfr is incorporated in the host genome and removal of MTX will not permit the cell line to eject the endogenous DHFR.

As shown in Table 1, populations which were selected and amplified to 1µM MTX according to the traditional prior art failed to amplify to higher productivity. These populations have ΔE index values of less than 3. However, cell populations with moderate productivity but a high ΔE index (>3) did amplify to higher productivity.

Also shown in Table 1, clones with high productivity were obtained using ΔE>3 from both pCIS-F8 (0.7–1.0 µU/c/d) and pCAIS-F8 (1.3–1.5 µU/c/d). Clones generated by pCAIS-F8 showed a significant 40–50% increase in productivity over those generated by pCIS-F8. These clones are stable and suitable for continuous production of Factor VIII under serum-free conditions.

Example 3. Continuous production of Factor VIII.

One of the high producing clones was grown to a cell density of $5-7 \times 10^5$ cells/mL in a 250 mL spinner in Joklik's minimum essential medium (Gibco) supplemented with 10% dialyzed fetal bovine serum. The culture was stirred at a speed of 100 r.p.m. and kept in a 37° C. incubator. The cells were then washed with Hank's buffered saline (Gibco), re-seeded in a 250 mL spinner flask at a density of $5 \times 10^5$ cells/mL in a serum-free production medium (Joklik's MEM supplemented with 5 µg/mL insulin, 25 µg/mL transferrin, 1 mg/mL human serum albumin and 15 mM $MgCl_2$), and kept at 37° C. After 24 hours, the culture fluid was harvested and assayed for Factor VIII production by the chromogenic Coatest method. The cells were then spun down, re-suspended in fresh serum-free production medium, and incubated at 37° C. for another 24 hours after which the same procedure is repeated at 24 hour intervals for 21 days. Throughout this production period the productivity of the cells was maintained in the range of 1.2–1.5 µU/c/d.

Given the above disclosure, variations will occur to those skilled in this field. For example, the arrangement of the augmenting sequence and the vectors of this disclosure could be used as vectors intended for gene therapy in humans. In the case of Factor VIII, the vector could be integrated into human liver cells. Accordingly, it is intended that the above examples should be construed as illustrative and that the scope of the invention disclosed should be limited only by the following claims.

What is claimed is:

1. A process of selecting a cell line having high heterologous protein productivity from a population of cells at least some of which may include an endogenous sequence for an amplifiable marker and some of which do not include the endogenous sequence for the same marker, comprising:
   A. co-transfecting the population of mammalian cells with DNA sequences coding for the heterologous protein and an amplifiable marker, and a DNA sequence encoding a selectable marker;
   B. further cloning the transfected cells into subpopulations in a medium containing a selective agent and selecting for such selectable marker resistant cells;
   C. assaying the selectable marker resistant cells for heterologous protein productivity;
   D. culturing said selectable marker resistant cells in media containing an amplifying agent, wherein the host cell includes the sequence for the amplifiable marker;
   E. establishing the amplifiability index AE for each cell population, said index being defined by the equation $$\Delta E = Y/X$$

wherein X is the productivity of cells before a first amplification, and Y is the productivity of cells after said first amplification;
   F. selecting and further amplifying cells with a ΔE index value of greater than 3, said amplifying step being performed in increasing amounts of amplifying agent; and
   G. selecting at least one cell line having high productivity from the cells of step F.

2. The method of claim 1 wherein said host cells comprise an expression vector having a sequence of double stranded DNA including:
   A. an augmenting sequence downstream of a promoter and upstream of a DNA encoding the amino acid sequence of the desired heterologous protein;
   B. DNA encoding the amino acid sequence of the desired protein downstream of said augmenting sequence; and
   C. DNA coding a polyadenylation sequence downstream of a transcription termination site.

3. The method of claim 2 wherein the augmenting sequence comprises in linear sequence a splice donor$_1$-intron$_1$-splice donor$_2$-intron$_2$-acceptor sequence operatively linked to the desired heterologous protein.

4. The method of claim 2 wherein the promoter is from the immediate early gene of human cytomegalovirus.

5. The method of claim 3 wherein the splice donor$_1$-intron$_1$ sequence is from the major late promoter region of adenovirus.

6. The method of claim 3 wherein the splice donor sequence is from the human cytomegalovirus.

7. The method of claim 3 wherein the intron$_2$-acceptor sequence is from the human immunoglobulin variable region.

8. The method of claim 1 wherein the DNA sequence coding for the heterologous protein encodes Factor VIII.

9. The method of claim 1 wherein the host cell is a human cell.

10. The method of claim 1 wherein the host cell is a human embryonic kidney cell.

11. The method of claim 1 wherein the host cell is a human embryonic kidney 293s cell.

12. A vector comprising in linear sequence a second promoter-first promoter-splice donor$_1$-intron$_1$-splice donor$_2$-intron$_2$-acceptor sequence operatively linked to a protein coding sequence.

13. The vector pCAIS-F8 chromosomally integrated into a mammalian cell.

14. The vector of claim 12 comprising a coding sequence for Factor VIII located downstream from the acceptor.

15. A mammalian cell line comprising the vector of claim 12 as an integrated chromosomal element.

16. A mammalian cell line comprising the vector of claim 14 as an integrated chromosomal element.

* * * * *